United States Patent [19]

Ulrich

[11] Patent Number: 4,484,819
[45] Date of Patent: Nov. 27, 1984

[54] REFLECTOMETER

[75] Inventor: Richard D. Ulrich, Provo, Utah

[73] Assignee: The United States of America as represented by the Secretary of the Navy, Washington, D.C.

[21] Appl. No.: 388,863

[22] Filed: Jun. 16, 1982

[51] Int. Cl.³ .......................................... G01N 21/47
[52] U.S. Cl. ................................................ 356/446
[58] Field of Search ............... 356/445, 446, 447, 448; 235/472

[56] References Cited

U.S. PATENT DOCUMENTS 3,327,583 6/1967 Vanderschmidt et al. ..... 356/446 X
3,421,821 1/1969 Alessi .............................. 356/445 X

FOREIGN PATENT DOCUMENTS 2414726 9/1979 France ................................. 356/445

Primary Examiner—Vincent P. McGraw
Attorney, Agent, or Firm—R. F. Beers; W. Thom Skeer; Kenneth G. Pritchard

[57] ABSTRACT

A portable reflectometer is made using a diffuse light and light sensor combination to measure reflectivity of solar wavelengths. A cadmium sulfide photocell is used as the light sensor connected to a voltage divider network which provides a linear response to an internal light source. The light shield is placed around the light source and the light sensor to limit detected light to only that reflected on the surface due to the diffuse light source. The invention is mounted in a hand-held gun configuration to provide easy use.

4 Claims, 2 Drawing Figures

REFLECTOMETER

BACKGROUND OF THE INVENTION

1. Field of the Invention

This invention is a light reflectometer. In particular, this invention is for a reflectometer that permits a direct measurement of absorptivity, α, of a surface.

2. Description of the Prior Art

Previously, absorptivity, α, has been guessed at or measured under laboratory conditions. There is no previous way of making a direct measurement of a surface in field conditions at any given time. No previously portable devices for measuring reflectivity and absorptivity are known.

SUMMARY OF THE INVENTION

A reflectometer is mounted in a tube with a voltage source, light, diffuser, and light sensor. The light sensor is shielded from the diffuse light caused by direct illumination. The tube is also configured to serve as a light shield or a separate device forming a light shield is mounted at one end of the tube. The tube is placed against this surface causing a portion of the surface to be deprived of all external light. Only light incident on this surface from the diffused light source within the tube is available. Light reflected from the enclosed surface is monitored by the light sensor which is a cadmium sulfide photocell. As the amount of reflected light increases, the photocell provides a linear increase in resistivity. The resistance present is read out on any appropriate device such as a liquid crystal display.

Accordingly, it is an object of the present invention to design a reflectometer which is small and easily transported. It is a further object of the present invention to remove the need to send samples of surfaces to laboratories for testing. It is a further object of the invention to provide sensor response to approximate the solar spectrum.

DETAILED DESCRIPTION OF THE INVENTION

Reflectivity, ρ, is the ratio of reflected radiation to the incident radiation. Absorptivity, α, is the ratio of the radiation which an object absorbs to the total radiation it receives. For an opaque body, one where the transmissivity is zero, the sum of reflectivity plus absorptivity is one, i.e. $\rho + \alpha = 1$. Thus, absorptivity can easily be determined if reflectivity is known.

While reflectivity of a surface for visible light may be easily judged, the infrared and ultraviolet radiation characteristics may not be similar. A material may have high reflectivity for visible and ultraviolet light and low reflectivity for infrared radiation. Thus, a measure of reflectivity requires an instrument that can measure all wavelengths of incoming solar radiation needed for accurate calculations.

Figure 1:
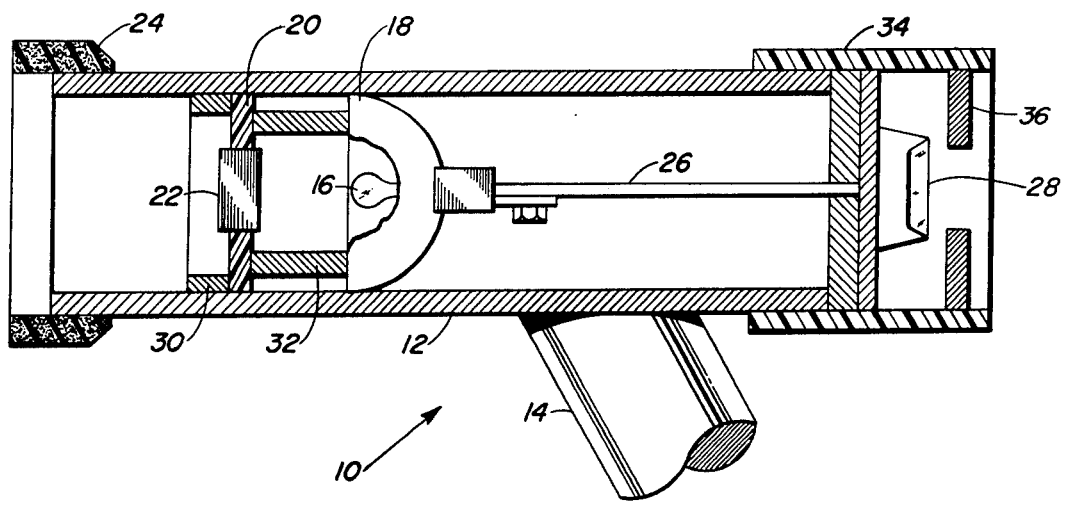
FIG. 1 is a cross-sectional view of the present invention.

FIG. 1 is a cross-sectional view of a reflectometer 10. Reflectometer 10 has an aluminum tube 12 which serves as a housing for the various components. A handle 14 is mounted to tube 12. A light 16 is mounted within a reflector 18 placed within tube 12. A diffuser 20 is placed in front of light 16. The diffused light is reflected from the surface to be measured and measured with a sensor 22 for reflected light intensity.

Light sensor 22 can be any suitable photocell. Ideal choice would provide a sensor 22 which approximates the solar system characteristics. Such a sensor is a cadmium sulfide photocell. Cadmium sulfide photocell is also usually calibrated because it changes internal resistance with the change in the intensity of light incident on it. A seal 24, such as foam rubber, is used to block external light from reaching the surface being tested. Seal 24 can be glued or otherwise mounted to tube 12. The amount of light striking sensor 22 varies linearly with reflectivity of the material being measured. Thus, the electrical output from sensor 22 varies in direct proportion to the reflectivity of the material being measured. A circuit board 26 amplifies the electrical output of sensor 22, converts it to a digital or other signal and displays it on a readout device 28. Readout device 28 can be a meter or liquid crystal display.

Sensor 22 and reflector 18 are held in fixed position within tube 12 by stopper 30 and spacer 32. The end of tube 12 is enclosed with a plastic housing 34 which contains a cover plate 36.

Figure 2:
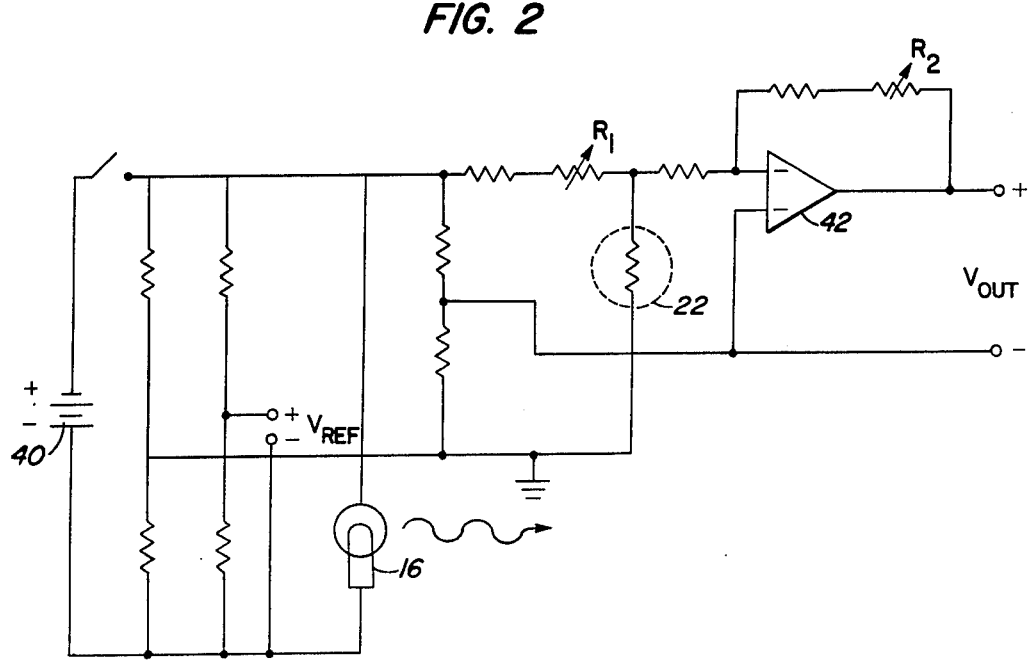
FIG. 2 is a circuit diagram of a circuit suitable for use in the present invention.

FIG. 2 shows a detailed schematic for circuit board 26. Sensor 22 is represented by a dashed circle. A standard battery 40, such as a 12-volt battery, is sufficient for light 16. As the internal resistance of sensor 22 changes, $V_{out}$ changes. The resistance of a cadmium sulfide sensor changes from 6,000 ohms to 16,000 ohms as the percent of reflected light varies from 0% to 100%. FIG. 2 is a voltage divider network.

The cadmium sulfide sensor 22 is placed in voltage divider network 26. As the resistance of CDS sensor 22 changes, the different output voltage, $V_{out}$, is produced from this network. To take advantage of this cadmium sulfide sensor change from 6,000 ohms to 16,000 ohms, it is desired to have a change in voltage of 1 volt over this resistance change. To determine the appropriate value for $R_1$, the value of $R_1$ can be set at either 2.7K ohms or 35K ohms. For reasons of stability, 2.7K ohms is preferred. For a 12-volt battery as battery 40, the resistor functions with an output voltage range of approximately 4–5 volts. An internal analog-to-digital converter is used normally with acceptable voltages between −2 and 2 volts. Therefore, the output voltage from the voltage divider network needs to be shifted and inverted such that approximately 4 volts represents 100% reflectivity and 5 volts represents 0% reflectivity. This is done by using an inverting amplifier 42 with unity gain and supplying a reference voltage $V_{ref}$ to the positive input of amplifier 42. Amplifier 42 can be a commercial 741 op amp. It is found that the reference voltage $V_{ref}$ is approximately 2.5 volts with this arrangement.

The reflectometer can be calibrated by placing it on a surface of high reflectivity, approximately 90%, and adjusting $R_1$ until the readout mechanism, such as a liquid crystal display, reads 90%. The instrument is then placed on a surface of known low reflectivity, approximately 10%, and $R_2$ is adjusted until the display reads 10%. Repetition of this procedure normally permits the reflectometer to slide into calibration.

Cadmium sulfide photocell sensors have a maximum sensitivity wavelength of approximately 0.55 microns. Response is approximately linear and has a response curve similar to that for solar radiation. Internal light source 16 has to be considered such that the sensitivity matches the solar energy spectrum. A good match is obtained assuming the light to have a color temperature of 2850° K. The total instrument response is equal to the sensor response times the light source spectral transmissivity. For zero instrument error, the instrument response should match the solar energy spectrum. In general, the back of sensor 22 is shielded so that no diffused light can reach the front of sensor 22 which receives reflected light.

It is obvious to those skilled in the art that numerous modifications of the above invention may be made.

What is claimed is:

1. A surface reflectometer comprising:

a tube with an open end;

a light source mounted within said tube;

a reflector mounted within said tube and around said light souurce, such that light from said light source is reflected towards said tube's open end;

a diffuser placed in said tube such that all of said light traveling towards said tube's open end must pass through said diffuser prior to reaching said tube's open end;

a light sensor placed in between said diffuser and said tube's open end, said light sensor only receiving light into said tube from said tube's open end;

an electrical circuit connected to said light sensor to measure the amount of light colected by said light sensor;

display means connected to said electrical circuit to display the amount of light received by said light sensor; and a light shield around said light tube's open end.

2. A surface reflectometer as described in claim 1 where said light sensor comprises a cadmium sulfide photocell sensor.

3. A surface reflectometer as described in claim 2 where said electrical circuit further comprises a voltage divider network connected to said cadmium sulfide cell.

4. A surface reflectometer as described in claim 3 where said display means comprises a liquid crystal display.

* * * * *